United States Patent [19]

Miller

[11] 4,430,113

[45] Feb. 7, 1984

[54] PLANT GROWTH REGULATOR COMPOSITIONS AND METHOD

[75] Inventor: Jack R. Miller, Greenfield, Ind.

[73] Assignee: Eli Lilly and Company, Indianapolis, Ind.

[21] Appl. No.: 295,437

[22] Filed: Aug. 24, 1981

Related U.S. Application Data

[63] Continuation-in-part of Ser. No. 148,115, May 9, 1980, abandoned.

[51] Int. Cl.$^3$ ............... A01N 43/54; A01N 41/00
[52] U.S. Cl. ............................... 71/92; 71/76; 71/103
[58] Field of Search ............... 71/76, 92, 103

[56] References Cited

U.S. PATENT DOCUMENTS

| | | | |
|---|---|---|---|
| 3,954,437 | 5/1976 | Gates et al. | 71/103 |
| 3,958,977 | 5/1976 | Prochaska et al. | 71/120 |
| 3,960,540 | 6/1976 | Crosby | 71/76 |
| 4,013,444 | 3/1977 | Fridinger | 71/76 |
| 4,194,899 | 3/1970 | Benefiel et al. | 71/76 |
| 4,288,242 | 9/1980 | Alt et al. | 71/76 |

OTHER PUBLICATIONS

Rogers et al.; "Performance of Soybean, etc.;" (1977), CA 87, No. 97152h.

*Primary Examiner*—Glennon H. Hollrah
*Attorney, Agent, or Firm*—Charles W. Ashbrook; Arthur R. Whale

[57] ABSTRACT

Compositions having as the essentially active ingredients a mixture of mefluidide and a pyrimidinemethanol growth regulator are disclosed. A method for controlling seedhead formation in turfgrasses employing the compositions is provided.

6 Claims, No Drawings

PLANT GROWTH REGULATOR COMPOSITIONS AND METHOD

CROSS REFERENCE TO RELATED APPLICATION

This is a continuation-in-part of Ser. No. 148,115, filed May 9, 1980 now abandoned.

BACKGROUND OF THE INVENTION

This invention concerns compositions employing known growth regulating agents. The compositions have improved properties over the respective ingredients, particularly in the regulation of seedhead formation in grasses.

The plant growth regulation art has now advanced to a stage in which compounds are available which can cause very specific and selective affects upon the growth and development of certain plants. For example, several agents are now in commercial use which either kill or greatly retard the growth of one or several grassy or broadleaf weeds, yet exhibit little or no adverse affect upon the growth and development of desired crop plants such as soybeans, cotton, corn and the like. The discovery and development of compounds which exhibit such selective herbicidal activity has virtually revolutionized the agriculture industry.

Since a great deal of efficacious selectivity often is associated with compounds which are useful due to their plant growth regulant activity, it is difficult or impossible to achieve a broad range of responses utilizing a single plant growth regulating agent. Consequently, the use of combinations of one or more selective agents sometimes is required in order to achieve a desired plant response.

The selectivity and limitations of growth regulator activity displayed by certain agents which affect the growth of various turfgrass species has severely limited the widespread commercial use of such agents. For example, mefluidide, a compound disclosed in U.S. Pat. No. 3,894,078, is a plant growth regulator which is effective in suppressing the seedhead formation in various turfgrass species. Mefluidide also causes a cessation of vegetative growth for a relatively short period of time when applied at adequate rates. In contrast, α-(1-methylethyl)-α-[4-trifluoromethoxyphenyl]-5-pyrimidinemethanol, a compound described in U.S. Pat. No. 4,002,628, is very effective in regulating the growth of various turfgrass species, but limited retardation of seedhead formation is manifested. As a result, the use of such growth regulator is restricted since turf having an abundance of seedheads is unsightly, even though the overall turf remains at a desirably short height.

With this invention, it has been discovered that a novel composition comprised of mefluidide and α-(1-methylethyl)-α-[4-trifluoromethoxyphenyl]-5-pyrimidinemethanol overcomes the many disadvantages associated with the use alone of the respective compounds. An object of the invention accordingly is to provide novel plant growth regulator compositions which are particularly useful as plant growth regulators for various turfgrasses. Additionally, the invention provides a method for regulating the growth of plants employing the novel compositions. The compositions of this invention provide a more immediate effect and a more prolonged growth retardation than is encountered with the use of either active ingredient alone. The compositions are particularly useful for the inhibition of seedhead formation in turfgrasses, including pasture grasses upon which domestic animals graze.

SUMMARY OF THE INVENTION

This invention relates to plant growth regulator compositions and to a method for controlling vegetative growth utilizing such compositions. The invention is more particularly directed to compositions comprised of, as a first component, mefluidide, a compound having the chemical name N-[2,4-dimethyl-5-(trifluoromethylsulfonylamino)phenyl]acetamide and defined by the formula

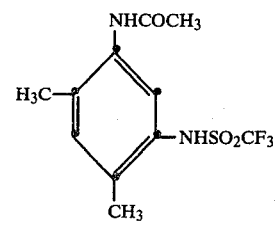

and as a second component the compound α-(1-methylethyl)-α-[4-(trifluoromethoxy)phenyl]-5-pyrimidinemethanol, a compound defined by the formula

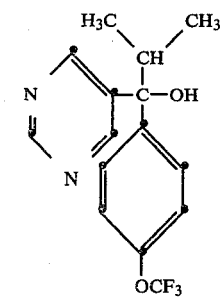

The compositions of this invention consist essentially of the above active ingredients, or suitable salts or derivatives thereof, in a ratio of about 1 part by weight of mefluidide to about 10 to about 80 parts by weight of the pyrimidinemethanol derivative. Preferred compositions comprise about 1 part of mefluidide to about 20 parts of the pyrimidinemethanol growth regulator.

Also provided by this invention is a method for controlling seedhead formation in turfgrass which comprises applying to the plants whose growth is to be regulated mefluidide and α-(1-methylethyl)-α-[4-(trifluoromethoxy)phenyl]-5-pyrimidinemethanol, or suitable derivatives thereof, which together are present in an amount effective for regulating plant growth. The composition will be applied so that mefluidide is present at a rate of about 0.025 to about 0.25 pounds per acre and the pyrimidinemethanol is present at a rate of about 0.5 to about 2.5 pounds per acre. The mefluidide is ideally present at about 0.2 pounds per acre and the pyrimidinemethanol at about 1.5 pounds per acre.

DETAILED DESCRIPTION OF THE INVENTION

To prepare the compositions of this invention, the active ingredients are normally blended together with a carrier in a suitable apparatus according to procedures well known to those skilled in the art of herbicidal and formulation chemistry. The active ingredients can be of a technical grade, for instance from about 85 to about 100 percent pure. If desired, salts or other suitable derivatives of the active ingredients can be employed. Commonly used salts of mefluidide include the diethanolamine salt. Horticulturally acceptable salts of the pyrimidinemethanol derivative include the acid addition salts made with acids such as hydrochloric or acetic acid.

The carrier utilized in preparing compositions of the invention may be any inert dry or liquid carrier. In the case of dry carriers, various types may be employed. Typical solid carriers and diluents include clay, diatomaceous earth, sand, talc, synthetic carriers and the like. Dry compositions may be blended and formulated as wettable powders and applied as sprays using water as a vehicle. Alternatively, the dry compositions may be formulated without a wetting agent and applied as a dust or in the form of granules or pellets.

The active ingredients of the composition can also be formulated as ready to use aqueous suspensions or oils or emulsifiable concentrates. They can additionally take the form of non-aqueous solutions or suspensions utilizing adjuvants and diluents such as xylene, toluene, acetone and the like.

As already pointed out, the active ingredients of this invention are known in the art and are readily synthesized by art-known methods. The mixture of active ingredients will be present, when formulated with the known carriers and excipients, in concentrations of about five percent by weight to about eighty percent by weight. If desired, suitable derivatives of the active ingredients can be employed to enhance formulation characteristics. A preferred form of mefluidide, for example, is as the diethanolamine salt. Such derivative is readily soluble in a vehicle such as water and lends itself to convenient application as an aqueous spray.

A preferred method for formulating and utilizing the compositions of this invention comprises tank-mixing individual formulations of mefluidide and α-(1-methylethyl)-α-[4-(trifluoromethoxy)phenyl]-5-pyrimidinemethanol. For example, the mefluidide can be formulated in water as the diethanolamine salt so that the solution is equivalent to about two pounds of mefluidide per gallon of solution. The α-(1-methylethyl)-α-[4-(trifluoromethoxy)phenyl]-5-pyrimidinemethanol can be formulated as a fifty percent wettable powder. The respective formulations can then be mixed and blended to uniformity at or near the site of application. The composition can be further diluted, for example by the addition of water or other suitable vehicle, so that the desired concentration of active ingredient is achieved, and the composition can be applied to plants which are to be growth regulated at a rate sufficient to effect the desired regulation.

The method for controlling seedhead formation in turfgrasses according to this invention comprises applying post-emergence to the plants to be growth regulated the composition provided herein in an amount sufficient to effect control of seedhead formation. In carrying out the method, the composition preferably will be applied post-emergence to the foliage of plants at a rate so that the mefluidide concentration is about 0.025 to about 0.25 pound per acre and the pyrimidinemethanol derivative is present at a rate of about 0.5 to about 2.5 pounds per acre. An especially preferred method comprises applying a growth regulating amount of a composition wherein mefluidide contacts the plants to be growth regulated when applied at a rate of about 0.1 to about 0.2 pounds per acre and the pyrimidinemethanol derivative contacts the plants when applied at a rate of about 1 to about 1.5 pounds per acre. If desired, the active components of the composition can be applied separately. All that is required is that the components be present at rates which, together, effect the desired control of seedhead formation.

The method of the invention is ideally suited to the growth regulation of various turfgrass species, including fine and course fescues, perennial bluegrasses such as Baron, Pennstar, Fylking; and ryegrasses, including Manhatten ryegrass. The compositions are surprisingly phytotoxic to undesired grasses such as large crabgrass, buckhorn plantain and related weedy species. The method also is well suited to the growth regulation of blends and mixtures of blends of various grass species, for instance any of the blends commonly employed in turf. The regulation of growth of turfgrasses is thus a preferred embodiment of the invention.

The regulation of growth of plants which can be achieved by employing the compositions and method of this invention offers many advantages over currently used growth regulation techniques. For example, the most common method of maintenance of highway right-of-ways which are seeded to turf requires the use of mechanical mowers and the like. Such methods are undesirable due to the increasing expense of machinery and manpower, as well as the fact that such method requires the use of oil based energy sources, which not only increases cost of right-of-way maintenance, but also adds to unfavorable environmental pollution. Moreover, mechanical mowing procedures near high-speed highways or other heavy traffic areas poses a particularly unsafe environment for both mower operators and motorists. Also, society is constantly looking toward ways of securing more time available for recreation and pleasure. Homeowners having a large turf area are required to spend a great deal of money and time in the maintenance of such areas. The present invention provides an economical alternative to these standard methods of maintenance.

The widespread use of either of the herbicidal agents employed in the present combinations has been prohibited due to their respective phytotoxic properties. As previously noted, the pyrimidinemethanol derivative fails to adequately and uniformly regulate seedhead formation in turfgrass species, and the presence of numerous seedheads in a turf greatly diminishes the aesthetic value of such turf area. Similarly, mefluidide, while effective in reducing seedhead formation, fails to retard growth of grasses beyond a period of about five to about seven weeks.

The compositions of the present invention provide a degree of seedhead inhibition of vegetation at rates and control levels which would not be expected or predicted from the teaching of the art. By virtue of the use of the compositions of the present invention, lower amounts of the active ingredients which have heretofore been required for adequate growth regulation are utilized. This advantage has resulted in an improved overall regulation of the growth of turf grass species, and additionally has resulted in a lowering of the levels of soil residue of the respective growth regulators. Moreover, the compositions of this invention effect excellent retardation of growth in height and seedhead formation of turfgrass species, while at the same time imparting no injury to such plant species so that an aesthetically pleasing turf appearance can be maintained. Also, reduction of seedheads in grasses commonly found in pastures permits grazing animals to obtain more nutritive value from the pasture grass than otherwise possible.

Having described in general terms the invention, the following exemplification of preferred embodiments will now be illustrated. The examples should not be construed as limiting the invention in any respect.

EXAMPLE 1

Tank-Mix Combination

Two pounds of a wettable powder formulation containing 50 percent by weight of α-(1-methylethyl)-α-[4-(trifluoromethoxy)phenyl]-5-pyrimidinemethanol were blended with 0.032 gallons of an aqueous suspension containing 2 pounds of mefluidide per gallon. The mixture was diluted with 50 gallons of water, and the solution was agitated to uniformity. The solution was sprayed uniformly over one acre of turfgrass, so that the pyrimidinemethanol concentration was one pound per acre and the mefluidide concentration was 0.064 pounds per acre.

EXAMPLE 2

Wettable Powder Formulation

| Ingredient | Amount (Pounds) |
|---|---|
| α-(1-methylethyl)-α-[4-trifluoromethoxy)phenyl]-5-pyrimidinemethanol technical grade, about 90 to about 98 percent pure | 10.0 |
| mefluidide, technical, about 95 percent pure | 2.5 |
| silicon dioxide, fumed silica | 10.0 |
| octylphenol-ethylene oxide blend wetting agent | 1.5 |
| | 24.0 |

The above ingredients are blended to uniformity in the dry state. The mixture can be air milled and passed through a screen to provide a free flowing powder of uniform particle size. The powder is diluted with water at the site of application and sprayed on turf foilage so that the concentration of the pyrimidinemethanol is about 1.0 pound per acre and that of the mefluidide is about 0.25 pounds per acre.

EXAMPLE 3

The compositions of this invention have been evaluated in greenhouse and open field tests designed to show growth regulator activity and crop injury. In a typical test, an established turf of a bluegrass blend comprised of 50% Baron, 25% Pennstar and 25% Fylking was grown in an open field on a level clay loam soil. The turf was mowed to a height of 2.5 inches and fertilized at one pound per 1000 square feet (18-5-9) prior to application of herbicide. The field was sectioned into plots measuring 3 feet by 10 feet. The composition of this invention was formulated by tank-mixing the individual ingredients, and application at various rates was accomplished by aqueous spray to foliage. Each concentration of the combination of this invention and the individual growth regulators was replicated three times. Analysis of growth regulation was made by visual inspection and comparison to an untreated control area. The degree of growth retardation was analyzed for the three replicates, and the values were averaged as a percent of plant growth inhibition relative to untreated control plots. Observations were made at various intervals post application. The results of one such test are presented below in Table I.

TABLE I

| Time of Observation (Days Post-Application) | Concentration of α-(1-methylethyl)-α-[4-trifluoromethoxy)phenyl]-5-pyrimidinemethanol (Lbs/A) | Mefluidide Concentration (Lbs/A) | | | |
|---|---|---|---|---|---|
| | | 0 | 0.0625 | 0.125 | 0.25 |
| 14 | 0 | 0 | 43 | 65 | 76 |
| 14 | 0.75 | 0 | 72 | 75 | 90 |
| 14 | 1.0 | 7 | 88 | 88 | 95 |
| 14 | 1.5 | 30 | 89 | 90 | 96 |
| 14 | 2.0 | 30 | 90 | 91 | 97 |
| 24 | 0 | 0 | 53 | 72 | 80 |
| 24 | 0.75 | 27 | 82 | 77 | 87 |
| 24 | 1.0 | 33 | 88 | 85 | 92 |
| 24 | 1.5 | 35 | 90 | 89 | 92 |
| 24 | 2.0 | 40 | 91 | 91 | 94 |
| 38 | 0 | 0 | 35 | 45 | 37 |
| 38 | 0.75 | 37 | 60 | 53 | 72 |
| 38 | 1.0 | 60 | 73 | 72 | 78 |
| 38 | 1.5 | 67 | 86 | 83 | 87 |
| 38 | 2.0 | 72 | 93 | 90 | 92 |
| 52 | 0 | 0 | 7 | 7 | 10 |
| 52 | 0.75 | 13 | 33 | 30 | 35 |
| 52 | 1.0 | 27 | 55 | 42 | 60 |
| 52 | 1.5 | 23 | 68 | 67 | 65 |
| 52 | 2.0 | 53 | 75 | 73 | 78 |

EXAMPLE 4

A study similar to that described in Example 3 was carried out to determine the efficacy and turfgrass tolerance of the tank-mixed combination of this invention when applied to the foliage of a bluegrass turf comprised of 50 percent Baron, 25 percent Fylking and 25 percent Pennstar. The results of the study are presented in Table II.

TABLE II

| Time of Observation (Days Post-Application) | Concentration of α-(1-methylethyl)-α-[4-trifluoromethoxy)phenyl]-5-pyrimidinemethanol (Lbs/A) | Mefluidide Concentration (Lbs/A) | |
|---|---|---|---|
| | | 0 | 0.25 |
| 17 | 0 | 0 | 98 |
| 17 | 0.5 | 58 | |
| 17 | 1.0 | 76 | |
| 17 | 2.0 | 93 | 100 |
| 35 | 0 | 0 | 81 |
| 35 | 0.5 | 66 | |
| 35 | 1.0 | 83 | |
| 35 | 2.0 | 94 | 98 |
| 41 | 0 | 0 | 69 |
| 41 | 0.5 | 55 | |
| 41 | 1.0 | 73 | |
| 41 | 2.0 | 93 | 98 |
| 51 | 0 | 0 | 55 |
| 51 | 0.5 | 48 | |
| 51 | 1.0 | 66 | |
| 51 | 2.0 | 91 | 90 |

EXAMPLE 5

By following the procedure of Example 3, the combination of this invention was evaluated on a turf of bluegrass and fine textured ryegrass comprised of a blend of Manhatten and Pelo Ryegrass, and a blend of Pennstar and Fylking bluegrass. As the data in Table III demonstrate, the composition of this provides excellent growth inhibition over a prolonged period when applied to plant foliage.

TABLE III

| Time of Observation (Days Post-Application) | Concentration of α-(1-methylethyl)-α-[4-trifluoromethoxy)phenyl]-5-pyrimidinemethanol (Lbs/A) | Mefluidide Concentration (Lbs/A) 0 | 0.25 |
|---|---|---|---|
| 17 | 0 | 0 | 90 |
| 17 | 0.5 | 62 | |
| 17 | 1.0 | 77 | |
| 17 | 2.0 | 92 | 100 |
| 35 | 0 | 0 | 63 |
| 35 | 0.5 | 52 | |
| 35 | 1.0 | 69 | |
| 35 | 2.0 | 85 | 98 |
| 41 | 0 | 0 | 50 |
| 41 | 0.5 | 45 | |
| 41 | 1.0 | 62 | |
| 41 | 2.0 | 82 | 97 |
| 51 | 0 | 0 | 50 |
| 51 | 0.5 | 43 | |
| 51 | 1.0 | 62 | |
| 51 | 2.0 | 78 | 90 |

EXAMPLE 6

The growth inhibitory efficacy of combinations of the invention against several bioassay species was determined by greenhouse experiments carried out as follows: Flats were filled with steamed Brookston silt loam soil. The soil was top watered and allowed to drain to field capacity. The individual flats were seeded in strips with Captan-treated large crabgrass, buckhorn plantain and Manhatten-perennial ryegrass. After seeding, the flats were top dressed with soil, watered at three-day intervals, and maintained in a greenhouse. After the three strips of bioassay species has emerged, strips of large crabgrass and buckhorn plantain were seeded in the same flats and top dressed with soil. The flats were treated with varying rates of mefluidide and α-(1-methylethyl)-α-[4-(trifluoromethoxy)phenyl]-5-pyrimidinemethanol, and the combinations thereof. After the growth regulators had been applied, the flats were held in a greenhouse for four weeks to allow plants to establish and develop and to allow toxicity symptoms to develop. The pre- and post-emergent growth regulator activity of the compounds was evaluated against the large crabgrass and buckhorn plantain species, while only the post-emergent activity against Manhatten ryegrass was evaluated.

In all cases, growth inhibition efficacy was determined by visual examination using a rating scale of 0 to 10, with 0 being no inhibition or normal growth, and 10 being 100% inhibition or no new growth. The code letters B, R and S were used to indicate burning, reduced germination and stunting respectively. The results of the assay are presented in Table IV.

TABLE IV

Mefluidide Concentration (Lbs/A)

Large Crabgrass

| Concentration of α-(1-methylethyl)-α-[4-trifluoromethoxy)phenyl]-5-pyrimidinemethanol (Lbs/A) | Post-Emergence | | | | Pre-Emergence | | | |
|---|---|---|---|---|---|---|---|---|
| | 0 | 0.0625 | 0.125 | 0.25 | 0 | 0.0625 | 0.125 | 0.25 |
| 0 | 0 | 0 | 2S | 2S | 0 | 0 | 0 | 2S |
| 0.0625 | 3S | 2S | 2S | 3S | 3S | 7RS | 4S | 6S |
| 0.125 | 3S | 3S | 3S | 3S | 4S | 5S | 5S | 7S |
| 0.25 | 4S | 3.5S | 3.5S | 3S | 5S | 6S | 5S | 6S |

Buckhorn Plantain

| (Lbs/A) | Post-Emergence | | | | Pre-Emergence | | | |
|---|---|---|---|---|---|---|---|---|
| | 0 | 0.0625 | 0.125 | 0.25 | 0 | 0.0625 | 0.125 | 0.25 |
| 0 | 0 | 0 | 0 | 0 | 0 | 0 | 0 | 0 |
| 0.0625 | 2S | 2S | 3S | 3S | 4S | 7RS | 7RS | 8RS |
| 0.125 | 3S | 3S | 4S | 4S | 8RS | 8RS | 7RS | 10 |
| 0.25 | 3S | 5S | 4S | 4S | 8RS | 9RS | 7RS | 9RS |

Manhatten Ryegrass

| Concentration of α-(1-methylethyl)-α-[4-trifluoromethoxy)phenyl]-5-pyrimidinemethanol (Lbs/A) | Post-Emergence | | | |
|---|---|---|---|---|
| | 0 | 0.0625 | 0.125 | 0.25 |
| 0 | 0 | 0 | 0 | 2BS |
| 0.0625 | 0 | 0 | 2S | 3BS |
| 0.125 | 0 | 0 | 2S | 3BS |
| 0.25 | 0 | 2BS | 2SB | 3BS |

The results demonstrate that the combinations of the invention are selectively more efficacious than the components against undesired weeds such as crabgrass and buckhorn plantain. The combinations accordingly are useful when applied pre-emergence in retarding the germination and growth of undesirable grass species such as crabgrass, while still providing growth inhibition to the desirable species.

EXAMPLE 7

Growth regulator efficacy also was determined in open field plots. Plots having an established turf comprised of 50% Baron, 25% Pennstar and 25% Flyking were treated with various concentrations of the respective components of the combination of the invention, and with the combination. Efficacy ratings were made thirty-eight days later by visual inspection, using a scale of zero to 100 percent, with zero percent being no turf inhibition and 100 percent being no new growth or 100% inhibition. The results of the field study are presented in Table V.

TABLE V

| Concentration of α-(1-methylethyl)-α-[4-tri-fluoromethoxy)phenyl]-5-pyrimidinemethanol (Lbs/A) | Mefluidide Concentration (Lbs/A) | | | |
| --- | --- | --- | --- | --- |
| | 0 | 0.0625 | 0.125 | 0.25 |
| 0 | 0 | 0 | 0 | 0 |
| 0.75 | 0 | 0 | 0 | 13 |
| 1.0 | 0 | 20 | 23 | 23 |
| 1.5 | 0 | 27 | 23 | 33 |
| 2.0 | 0 | 40 | 37 | 43 |

EXAMPLE 8

The synergistic activity of the components required by the composition of this invention was determined by observation of turf grass seedhead inhibition in open field plots. Established turf comprised of a blend of deluxe bluegrasses, Baron, Flyking and Pennstar as described in Example 7 was employed for the test. Plots measuring 3 feet by 10 feet were employed, and three replicates were used for each evaluation. The field plots had a level topography, and were irrigated as needed by a total sprinkler system.

Mefluidide, as the commercial 25 formulation, and the pyrimidinemethanol as a 50 percent wettable powder formulation, were mixed with water and sprayed individually onto turf plots at varying rates of active ingredient. The combinations of the respective components provided by this invention were prepared by tank mixing the individual components.

The degree of seedhead control in the form of inhibition in each plot caused by the individual components and the combination was determined by visual inspection and comparison of each treated plot against and other treated plots and against a non-treated control plot. The seedhead inhibition was rated on a scale of zero to ten, with zero being assigned to the control plots and being equivalent to no seedhead inhibition, and ten being equivalent to one hundred percent control, or total inhibition of seedhead formation. Observations were made about one month post application on each of three replicated plots for each application rate employed. The individual observations for the replicates were pooled to arrive at a mean percentage of seedhead inhibition. Table VI which follows presents the results of this field study.

TABLE VI

| Turf Grass Seedhead Inhibition | | | | | |
| --- | --- | --- | --- | --- | --- |
| α-(1-methylethyl)-α-04-(trifluoromethoxy)-phenyol-5-pyrimidine methanol (pounds per acre) | Mefluidide (pounds per acre) | | | | |
| | 0 | 0.031 | 0.0625 | 0.125 | 0.25 |
| 0 | 0 | 0 | 17 | 53 | 57 |
| 0.5 | 0 | 43 | 43 | 87 | 98 |
| 0.75 | 0 | 40 | 63 | 97 | 100 |
| 1.0 | 0 | 53 | 50 | 88 | 100 |
| 1.5 | 0 | 82 | 80 | 95 | 100 |
| 2.0 | 17 | 73 | 87 | 98 | 100 |

The results of the various tests carried out utilizing the compositions provided by this invention demonstrate that the compositions are surprisingly effective in maintaining turf grasses at desirable levels of growth for a prolonged period of time. In particular, when applied to the foliage of turf which has been manicured to an aesthetically pleasing growth pattern, the compositions of the invention are effective in maintaining the aesthetic nature of the turf by retarding the linear growth of the plants, while at the same time eliminating the excessive and unsightly accumulation of seedheads. Moreover, the desired growth regulation is achieved with concentrations of the composition which do not adversely affect aesthetic values associated with a turf. In particular, the compositions as employed by the method of this invention maintain a turf with its natural amount of coloration, so that no unsightly browning or chlorosis is encountered. Use of the compositions according to this invention accordingly provides an economical means for maintaining a desired turf appearance throughout an entire growing season by repeated applications from 1 to about 4 times per growing period, or as needed by the particular species of turf being regulated, as well as the climatic condition of sun and water which affect the growth of vegetation. The combinations according to this invention permit the use of the components at concentrations lower than would be expected for the degree of growth regulation encountered. Additionally, use of the compositions according to this invention permits the continued regulation of growth of desirable turfgrass species such as bluegrasses and the like while at the same time inhibiting the emergence and development of undesired turf weed species such as crabgrass, buckhorn plantain, dandelion, white clover and the like. The compositions provided herein are particularly valuable for the control of seedheads in grasses, including pasture grasses such as rye and timothy. This reduction in grass seedheads permits grazing cattle and the like to remain on pasture for longer periods of time and to obtain more nutritive value from the grass.

I claim:

1. A composition suitable for controlling seedhead formation in turfgrasses consisting essentially of about 0.031 to about 0.125 part by weight of mefluidide and about 0.5 to about 2.0 parts by weight of α-(1-methylethyl)-α-[4-(trifluoromethoxy)phenyl]-5-pyrimidinemethanol, or a nonphytotoxic acid addition salt thereof.

2. The composition of claim 1 consisting essentially of about 0.0625 part by weight of mefluidide and about 1.0 part by weight of α-(1-methylethyl)-α-[4-(trifluoromethoxy)phenyl]-5-pyrimidinemethanol.

3. The composition of claim 1 wherein said composition contains an inert carrier for the mixture of active ingredients.

4. The composition of claim 2 wherein said composition contains an inert carrier for the mixture of active ingredients.

5. A method for controlling seedhead formation in turfgrasses comprising applying to the locus where seedhead control is desired the composition of claim 1 such that mefluidide is present at about 0.031 to about 0.125 pounds per acre and α-(1-methylethyl)-α-[4-(trifluoromethoxy)phenyl]-5-pyrimidinemethanol is present at about 0.5 to about 2.0 pounds per acre.

6. The method of claim 5 wherein mefluidide is present at a rate of about 0.0625 pounds per acre and α-(1-methylethyl)-α-[4-(trifluoromethoxy)phenyl]-5-pyrimidinemethanol is present at about 1.0 pounds per acre.

* * * * *